(12) United States Patent
Propp

(10) Patent No.: US 7,780,634 B2
(45) Date of Patent: Aug. 24, 2010

(54) CUSHIONED MEDICAL SECUREMENT DEVICE

(75) Inventor: Donald J. Propp, Dewitt, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 112 days.

(21) Appl. No.: 12/256,809

(22) Filed: Oct. 23, 2008

(65) Prior Publication Data

US 2009/0048564 A1 Feb. 19, 2009

Related U.S. Application Data

(62) Division of application No. 11/233,799, filed on Sep. 24, 2005, now abandoned.

(51) Int. Cl.
*A61M 5/32* (2006.01)
(52) U.S. Cl. .................. 604/180; 604/304; 604/305; 604/308; 602/41; 602/57; 602/58
(58) Field of Classification Search .......... 604/174, 604/179, 180, 304–305, 307–308, 344–345; 602/41–43, 46, 52, 54, 57–58
See application file for complete search history.

(56) References Cited

U.S. PATENT DOCUMENTS

| 4,564,010 | A | * | 1/1986 | Coughlan et al. ........... 604/307 |
| 4,600,001 | A | | 7/1986 | Gilman |
| 4,614,183 | A | * | 9/1986 | McCracken et al. ......... 128/846 |
| 5,008,110 | A | * | 4/1991 | Benecke et al. ............. 424/448 |
| 6,159,497 | A | * | 12/2000 | LaPrade et al. ............. 424/448 |
| 6,224,571 | B1 | * | 5/2001 | Bierman ..................... 604/174 |
| 6,419,660 | B1 | * | 7/2002 | Russo ........................ 604/180 |
| 6,689,104 | B2 | * | 2/2004 | Bierman ..................... 604/174 |
| 2004/0034330 | A1 | | 2/2004 | Bierman et al. |
| 2004/0204684 | A1 | * | 10/2004 | Bierman ..................... 604/174 |
| 2005/0197628 | A1 | | 9/2005 | Roberts et al. |

* cited by examiner

*Primary Examiner*—Nicholas D Lucchesi
*Assistant Examiner*—Quynh-Nhu H Vu
(74) *Attorney, Agent, or Firm*—Fildes & Outland, P.C.

(57) ABSTRACT

A cushioned medical securement device for cushioning and securing a patient medical device includes a laterally and longitudinally extending pad. The pad has an adhesive coated first side surface for adhering to the patient medical device and an opposing adhesive coated second side surface for adhering to a patient's skin. A first release liner is removably mounted on the first side surface. The first release liner has a first liner peel release value. A second release liner is removably mounted on the second side surface. The second release liner has a second liner peel release value that is greater than the first liner peel release value.

4 Claims, 4 Drawing Sheets

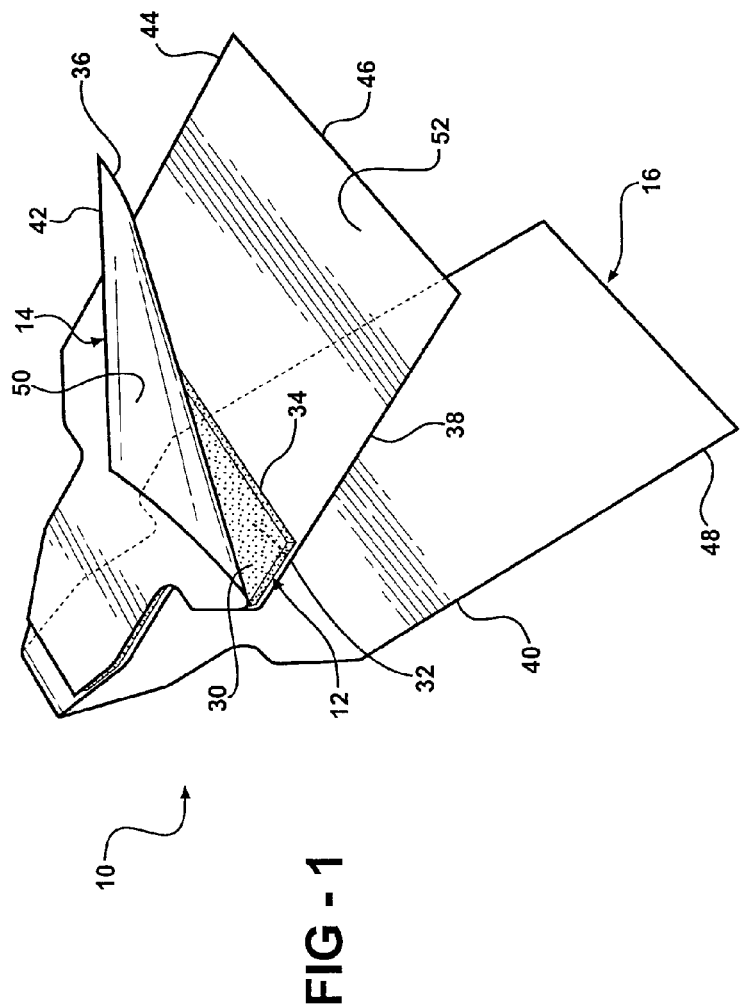
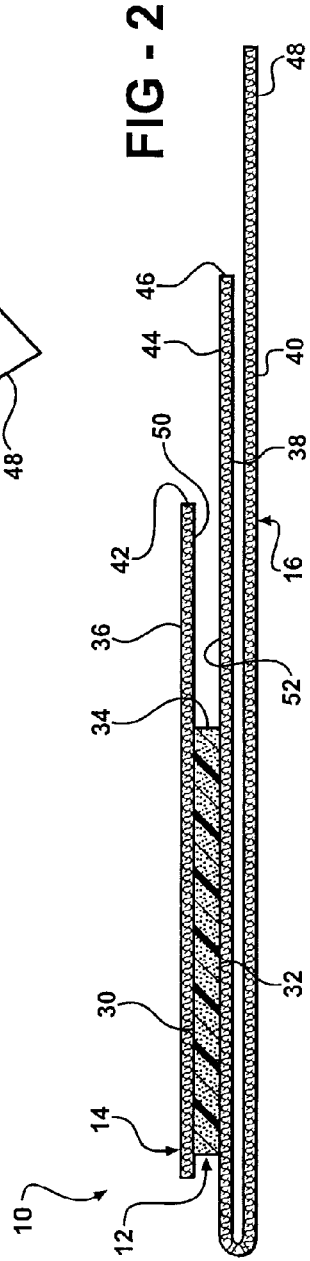

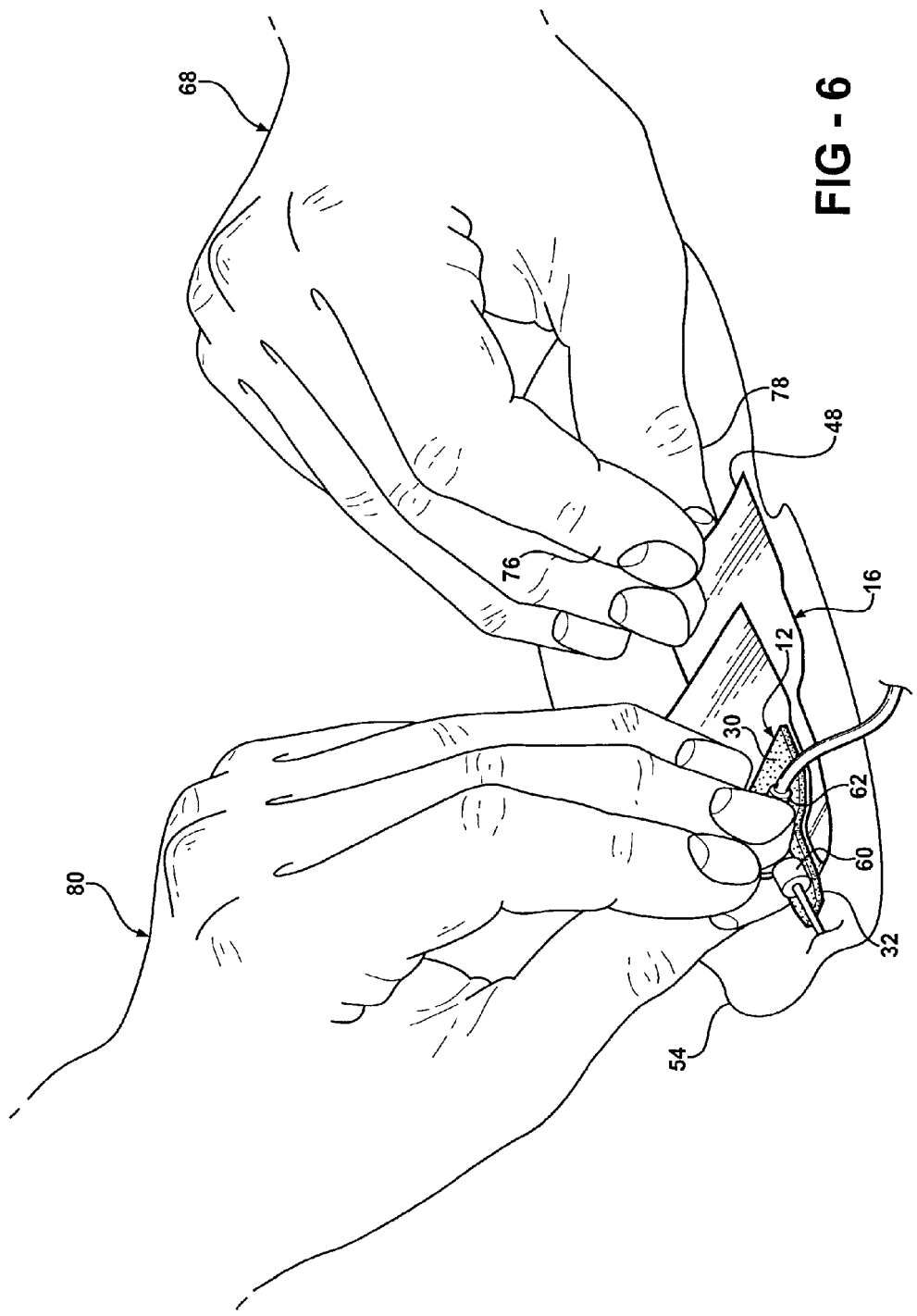

CUSHIONED MEDICAL SECUREMENT DEVICE

CROSS-REFERENCE TO RELATED APPLICATION

This application is a division of U.S. application Ser. No. 11/233,799 filed Sep. 24, 2005.

TECHNICAL FIELD

This invention relates to medical cushions, and more particularly to a device and method for cushioning and securing a patient medical device.

BACKGROUND OF THE INVENTION

In the medical field, it is known that patient medical devices such as catheters (and their associated hubs), medical connectors, IV extension sets, medical tubing, and the like, must be secured to a patient to limit or prevent disturbance, movement, or dislodgement of the medical devices. For example, once a catheter is introduced into a patient's vein, it is necessary to stabilize and secure the catheter to prevent movement or dislodgement of the catheter. Any movement of the catheter could work the catheter loose or create an in-and-out or up-and-down catheter tip movement, which can cause blood vessel wall irritation or damage. As a result, an unstabilized catheter is generally a source of discomfort and potential infection for a patient.

Further, the hard edges of patient medical devices, when pressed and secured directly against a patient's bare skin, can be a source of discomfort to the patient. This is especially true when patient medical devices are kept secured to a patient for days or more.

Conventionally, patient medical devices such as catheters and the like are secured by taping the catheter hub and associated connectors, tubings, and/or extension sets directly against the patient's skin. This method, however, has numerous deficiencies, including insufficient securement and stabilization of the patient medical devices as well as patient discomfort.

Furthermore, an acute issue in securing patient medical devices is the lack of free hands to perform the procedure. For example, when a health care provider such as a nurse introduces a catheter into a patient's vein, the nurse must use one hand to hold the catheter in the vein until the catheter is secured. Otherwise, the catheter will dislodge from the vein. This leaves the nurse with only one free hand to manipulate the securement device, e.g. tape, in order to secure the catheter. This makes the securement procedure tedious and difficult, and can lead to insufficient and inaccurate securement of patient medical devices.

SUMMARY OF THE INVENTION

The present invention provides a device and method for cushioning and securing a patient medical device against a patient's skin. The cushioned securement device provides both cushioning and stabilization of the patient medical device for maximum patient comfort. The method of applying the cushion can be accomplished solely with the use of one hand of a health care provider, leaving the provider's other hand free to grasp and secure the medical device during the cushion application process.

More particularly, a cushioned securement device for patient medical devices according to the present invention includes a laterally and longitudinally extending pad. The pad has an adhesive coated first side surface for adhering to the patient medical device and an opposing adhesive coated second side surface for adhering to a patient's skin. A first release liner is removably mounted on the first side surface. The first release liner has a first liner peel release value. A second release liner is removably mounted on the second side surface. The second release liner has a second liner peel release value that is greater than the first liner peel release value.

In a specific embodiment, the first release liner may extend longitudinally beyond an edge of the pad to form a first liner tab. The second release liner may extend longitudinally beyond the edge of the first liner tab to form at least one second liner tab. The second release liner may be a folded release liner. The folded second release liner may include an inner layer contacting said second side surface and extending longitudinally beyond the edge of the first liner tab to form an inner second liner tab. The folded second release liner may further include an outer layer folded over and continuous with the inner layer, the outer layer extending longitudinally beyond the edge of the inner second liner tab to form an outer second liner tab.

The first release liner may have a first siliconized side contacting the first side surface of the pad. The second release liner may have a second siliconized side contacting the second side surface of the pad. The first siliconized side may have more silicon disposed thereon than the second siliconized side.

Optionally, the pad may be generally T shaped and may be a foam pad or similar.

In an alternative embodiment of the present invention, a method is provided for cushioning and securing a patient medical device. The method includes providing a laterally and longitudinally extending cushioning pad. The cushioning pad includes a first release liner removably mounted on an adhesive coated first side surface of the pad and a second release liner removably mounted on an opposing adhesive coated second side surface of the pad. The first release liner has a first liner peel release value and the second release liner has a second liner peel release value. The second liner peel release value is greater than the first liner peel release value. First, solely the first release liner is peeled off the pad to expose the first side surface. The pad is then placed between the medical device and a patient's skin with the exposed first side surface facing the medical device. Next, the first side surface is adhered to the medical device, by touching it to the device with a small force. The second release liner is then peeled off the pad and out from under the pad by pulling on the outer second liner tab, without raising the medical device, to expose the second side surface. Finally, the second side surface is adhered to the patient's skin.

In a specific embodiment of the method, the first release liner may be peeled off the pad solely through the use of a user's first hand. Prior to adhering the first side surface to the medical device, the medical device may be raised slightly, solely through the use of the user's second hand. The pad may be placed between the slightly raised medical device and the patient's skin solely through the use of the user's first hand. The second side may be slid directly on patient's skin without sticking or hang up, because the second release liner is still disposed on the second side surface. The second release liner may be pulled out/peeled off the pad via a rolling V-folded liner, solely through the use of the user's first hand. A longitudinally extending second liner tab of the second release liner may be grasped with a pair of first and second fingers of the user's first hand, and the second release liner may be peeled off the pad with the same pair of fingers of the user's first hand.

These and other features and advantages of the invention will be more fully understood from the following detailed description of the invention taken together with the accompanying drawings.

BRIEF DESCRIPTION OF THE DRAWINGS

In the drawings:

FIG. 1 is a perspective view of a cushioned medical securement device in accordance with the present invention;

FIG. 2 is a side view of a cushioned medical securement device in accordance with the present invention;

FIG. 6 is an environmental view of the cushioned medical securement device of FIG. 5 illustrating removal of a second release liner of the pad for adhering a second side surface of the pad to a patient's skin.

DETAILED DESCRIPTION OF THE INVENTION

Figure 3:
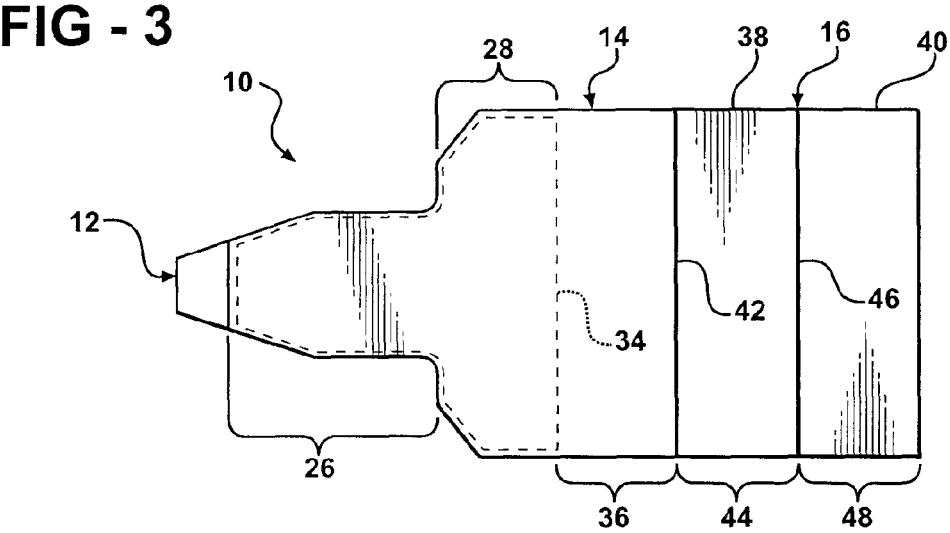
FIG. 3 is a plan view of a cushioned medical securement device in accordance with the present invention.

Referring to the drawings in general, and particularly to FIGS. 1, 2, and 3, numeral 10 generally indicates a cushioned medical securement device in accordance with the present invention. The cushioned medical securement device 10 includes a pad 12 sandwiched between a removable first release liner 14 and a removable second release liner 16. As will be described in greater detail herein, the cushioned securement device 10 is designed to be applied between a patient and a medical device associated with a patient (best shown in FIGS. 4 through 6) solely through the use of a health care provider's (or other user's) single hand. For illustrative purposes, a health care provider will herein be referred to as a nurse. Once applied, the cushioned securement device 10 secures the medical device to the patient and provides cushioning to maximize patient comfort.

More particularly, a cushioned medical securement device 10 includes a laterally and longitudinally extending pad 12. The pad 12 may be generally T-shaped and may have a longitudinally extending leg portion 26 and a laterally extending bar portion 28, which together form the pad's T shape. The pad, however, may have any other shape, such as a square shape, rectangular shape, circular shape, X shape, etc. One skilled in the art would recognize that any laterally and longitudinally extending pad 12 is within the scope of the invention so long as the overall shape adequately provides for cushioning and securement. The pad may be made of foam or other resilient materials such as rubber, silicone, polymers, or similar. The pad has an adhesive coated first side surface 30 for adhering to a patient medical device and an opposing adhesive coated second side surface 32 for adhering to a patient's skin.

The first release liner 14 is removably mounted on the first side surface 30. The first release liner 14 has a first liner peel release value. The second release liner 16 is removably mounted on the second side surface 32. The second release liner 16 has a second liner peel release value that is greater than the first liner peel release value.

The first release liner 14 may be of a size and shape to cover the entire first side surface 30 and extend laterally beyond a rear edge 34 of pad 12 to form a first liner tab 36. The second release liner 16 may be folded and may include an inner layer 38 mounted on and covering the pad's second side surface 32 and an outer layer 40 folded over and continuous with the inner layer 38. The inner layer 38 may extend longitudinally beyond a rear edge 42 of the first liner tab 36 to form an inner second liner tab 44. The outer layer 40 may extend longitudinally beyond a rear edge 46 of the inner second liner tab 44 to form an outer second liner tab 48. The inner layer 38 and outer layer 40 may generally have a similar shape. Prior to the use of the pad 12, the first and second release liners 14, 16 are mounted on respective sides 30, 32 of the pad 12.

Though the second release liner 16 is illustrated as being folded into an inner and outer layer 38 and 40, one would recognize that a single layer second release liner is also within the scope of the invention. Moreover, the inner and outer layers 38 and 40 need not be of unequal lengths.

The first release liner 14 may have a first release liner siliconized side 50 disposable on the first side surface 30 of the pad 12. The inner layer 38 of the second release liner 16 may have a second release liner siliconized side 52 disposable on the second side surface 32 of the pad 12. The first liner and second liner siliconized sides 50, 52, however, may be coated with a material similar to but different than silicone. Each siliconized side 50 and 52 of release liners 14 and 16 respectively may have a precisely controlled amount of silicone disposed thereon, such that the first siliconized side 50 contains more silicone than the second siliconized side 52.

The amount of force required to separate, or otherwise remove, each release liner 14 and 16 from an adhesive surface is known as the peel release value and is inversely proportional to the amount of silicone disposed on each siliconized side 50 and 52. Since the first siliconized side 50 has more silicone than the second siliconized side 52, the liner 14 has a lower peel release value than liner 16. Accordingly, if a user pulls on both liners 14 and 16 simultaneously, the first release liner 14 will peel off the first side surface 30 of the pad 12 before the second release liner 16 will peel off of the second side surface 32 of pad 12.

Advantageously, the feature of differential peel release values enables a user to remove release liners from and apply pad 12 between a patient and a medical device disposed about the patient with only one hand. This leaves the user's other hand free to hold the medical device so that it does not move relative to the patient. Most conventional pads, cushions, securement devices, etc. require two hands to remove release liners covering adhesive portions of these devices. Though the peel release values of liners 14 and 16 are described herein as being regulated by the amount of silicone disposed on each associated siliconized side 50 and 52, it is within the scope of this invention to use any suitable material to regulate the peel release values of the liners 14 and 16. Further, the absolute amounts of peel values can vary over a wide range so long as there is adequate differential amounts between the two peel values.

Figure 4:
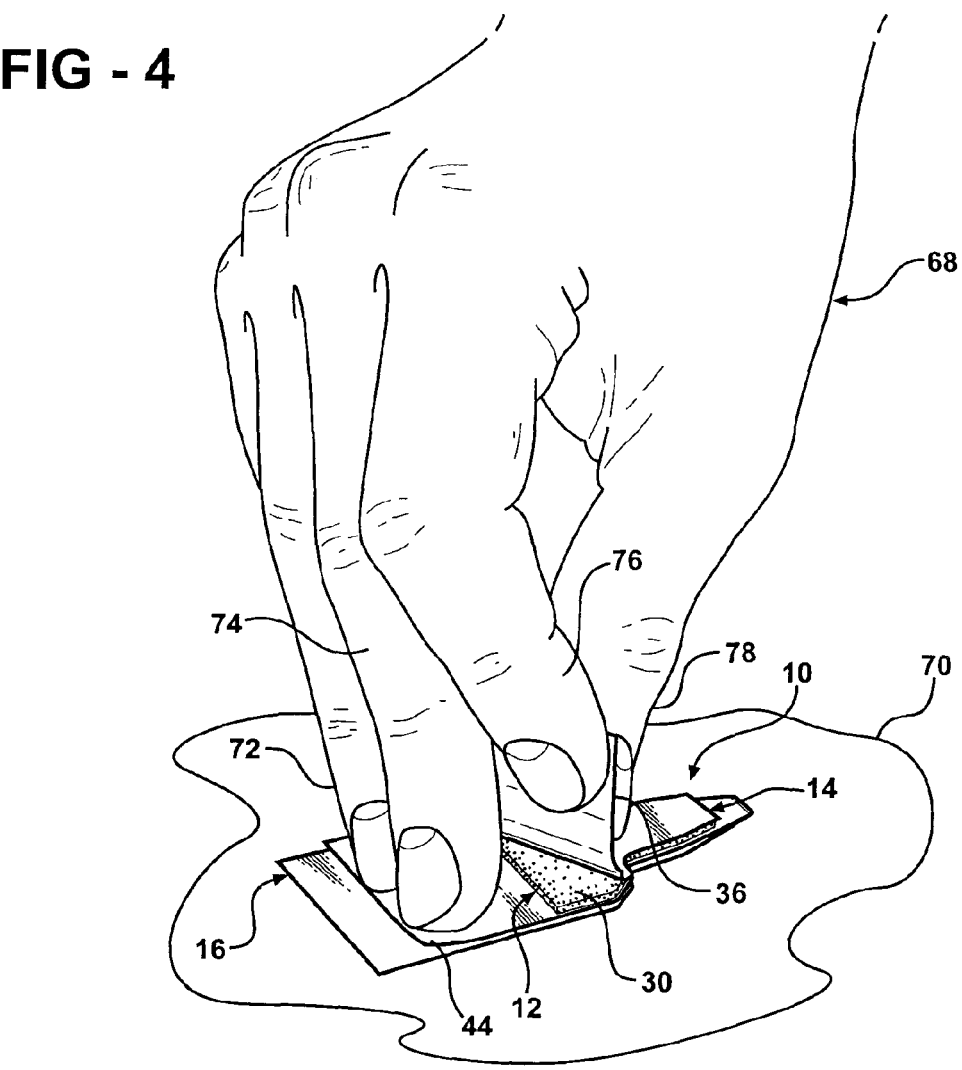
FIG. 4 is an environmental view of the cushioned medical securement device of FIG. 1 illustrating removal of a first release liner of a pad of the device.
Figure 5:
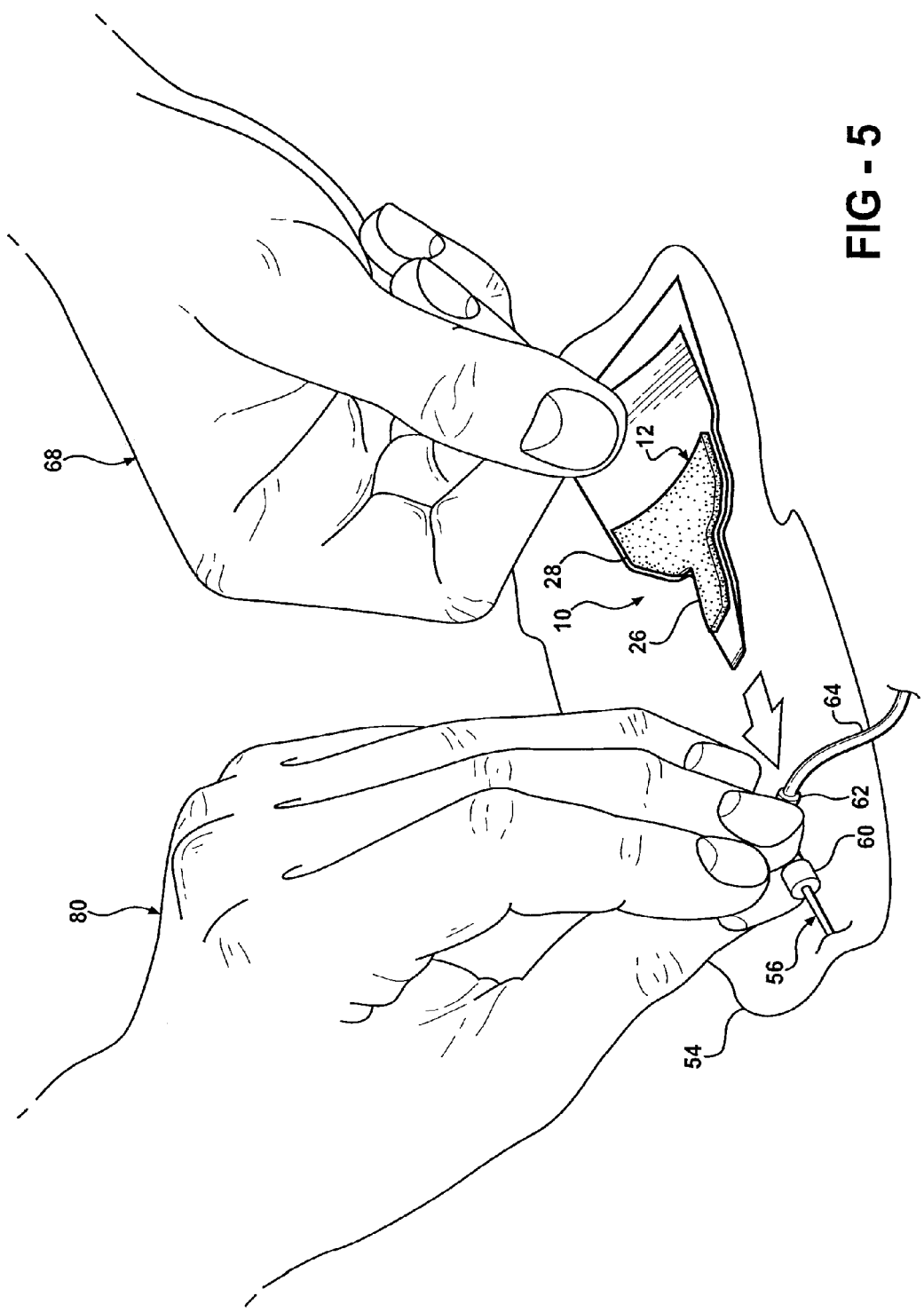
FIG. 5 is an environmental view of the cushioned medical securement device of FIG. 4 illustrating sliding under and adhering an exposed first side surface of the pad to a medical device.

FIGS. 4, 5 and 6 illustrate a method of applying the cushioned medical securement device 10. For illustrative purposes, the cushioned securement device 10 is shown being applied between a patient's skin 54 and a catheter 56. The catheter 56 includes a catheter hub 60. In this case, the hub 60 is connected to angled IV connector 62, which is further coupled to medical tubing 64. Though the cushioned securement device 10 is described as cushioning and securing an angled connector 62, the cushioned securement device 10 may be utilized to cushion and secure other combinations of catheters, IV connectors, or other patient medical devices. For example, the cushioned securement device 10 may be utilized with straight IV connectors and/or extension sets.

Referring to FIG. 4, once the catheter 56 has been inserted into the patient's skin 54, a nurse will use a first hand 68 to place the cushioned securement device 10 on a secure surface 70 with the first release liner 14 facing upwards. Solely with hand 68, the nurse will then press down on tab 44 of the second release liner 16 with one or more fingers 72 and 74, while simultaneously grasping and pulling on tab 36 of the first release liner 14 with at least a pair of fingers and/or thumb 76, 78. Because the peel release value of first liner 14 is less than the peel release value of second liner 16, the first liner 14 will be peeled off pad 12 to expose the first side surface 30 while the second liner 16 will remain in contact with the second side surface 32 (shown in FIG. 2).

Referring to FIG. 5, the nurse's second hand 80 is utilized to hold the catheter hub 60 and connector 62 in a slightly raised position. With first hand 68, the nurse then places the pad 12 between the raised catheter hub 60 and the patient's skin 54 with the exposed first side surface 30 facing catheter hub 60. Next the catheter hub 60 and connector 62 are adhered to the adhesive coated first side surface 30 by pressing the leg portion 26 of pad 12 against the catheter hub 60 and pressing the bar portion 28 of pad 12 against the connector 62.

Referring to FIG. 6, once the catheter hub 60 and connector 62 are securely adhered to the first side surface 30, the nurse grasps the extended tab 48 of second liner 16 with finger/thumb pair 76, 78 of the nurse's first hand 68. The nurse then pulls on tab 48 to peel the second liner 16 off pad 12 to expose the adhesive coated second side surface 32. Finally, the nurse presses down on catheter hub 60 and connector 62 to securely adhere the second side surface 32 to the patient's skin 54.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A method of cushioning and securing a patient medical device, the method comprising the steps of:
   providing a laterally and longitudinally extending cushioning pad including a first release liner removably mounted on an adhesive coated first side surface of said pad and a second release liner removably mounted on an opposing adhesive coated second side surface of said pad, said first release liner having a first liner peel release value and said second release liner having a second liner peel release value, said second liner peel release value being greater than said first liner peel release value;
   peeling solely said first release liner off said pad to expose said first side surface; placing said pad between said medical device and a patient's skin with said exposed first side surface facing said medical device;
   adhering said first side surface to said medical device;
   peeling said second release liner off said pad to expose said second side surface;
   adhering said second side surface to said patient's skin; and
   peeling said first release liner off said pad solely through the use of a user's first hand;
   prior to adhering said first side surface to said medical device, raising said medical device solely through the use of said user's second hand.

2. The method of claim 1 comprising: placing said pad between said raised medical device and said patient's skin solely through the use of said user's first hand.

3. The method of claim 1 comprising:
   peeling said second release liner off said pad solely through the use of a user's first hand.

4. The method of claim 3 comprising:
   grasping a longitudinally extending second liner tab of said second release liner with a pair of first and second fingers of said user's first hand; and
   peeling said second release liner off said pad with said pair of fingers of said user's first hand.

\* \* \* \* \*